United States Patent
Meyer et al.

(10) Patent No.: US 7,452,077 B2
(45) Date of Patent: Nov. 18, 2008

(54) IMAGE ADJUSTMENT DERIVED FROM OPTICAL IMAGING MEASUREMENT DATA

(75) Inventors: Scott Meyer, Livermore, CA (US);
Xunchang Chen, Pleasanton, CA (US);
Rodney P. Chin, Carson City, NV (US)

(73) Assignee: Carl Zeiss Meditec, Inc., Dublin, CA (US)

( * ) Notice: Subject to any disclaimer, the term of this patent is extended or adjusted under 35 U.S.C. 154(b) by 0 days.

(21) Appl. No.: 11/511,651

(22) Filed: Aug. 29, 2006

(65) Prior Publication Data
US 2008/0055543 A1    Mar. 6, 2008

(51) Int. Cl.
*A61B 3/10* (2006.01)
*A61B 3/14* (2006.01)

(52) U.S. Cl. .................. 351/205; 351/210
(58) Field of Classification Search .......... 351/205, 351/208–210, 212
See application file for complete search history.

(56) References Cited

U.S. PATENT DOCUMENTS

| | | | | |
|---|---|---|---|---|
| 5,491,524 | A * | 2/1996 | Hellmuth et al. | 351/212 |
| 6,053,613 | A * | 4/2000 | Wei et al. | 351/205 |
| 6,220,706 | B1 | 4/2001 | Foley | 351/209 |
| 6,325,512 | B1 | 12/2001 | Wei | 351/209 |
| 6,669,340 | B2 | 12/2003 | Percival et al. | 351/208 |
| 6,741,948 | B2 | 5/2004 | Hauger et al. | 702/152 |
| 6,749,302 | B2 | 6/2004 | Percival et al. | 351/208 |
| 7,001,377 | B1 | 2/2006 | Li | 606/5 |
| 7,044,602 | B2 | 5/2006 | Chernyak | 351/208 |
| 2003/0160943 | A1 * | 8/2003 | Xie et al. | 351/209 |
| 2005/0018133 | A1 * | 1/2005 | Huang et al. | 351/205 |
| 2006/0164653 | A1 | 7/2006 | Everett et al. | 356/479 |
| 2006/0279698 | A1 * | 12/2006 | Muhlhoff et al. | 351/208 |

OTHER PUBLICATIONS

D.X. Hammer et al., "Active retinal tracker for clinical optical coherence tomography systems," *Journal of Biomedical Optics*, vol. 10, No. 2, Mar./Apr. 2005, pp. 024038-1 thru 0240389-11.
R. Krueger et al., book entitled Wavefront Customized Visual Correction: The Quest for Super Vision II, published by Slack Incorporated, Chapter 24, entitled "Eye Tracking and Alignment in Refractive Surgery: Requirements for Customized Ablation" (authored by Natalie Taylor et al.), published 2004, 11 pages in length.

* cited by examiner

*Primary Examiner*—Scott J. Sugarman
*Assistant Examiner*—Dawayne A Pinkney
(74) *Attorney, Agent, or Firm*—Stallman & Pollock LLP

(57) ABSTRACT

A method and apparatus for imaging within the eye is provided whereby a component of eye position is detected using optical imaging data. Tracking eye position over time and correctly registering imaging data for scan locations or using eye position to detect decentration achieves improved imaging. In one embodiment, essentially perpendicular B-scans are imaged sequentially and the corneal arc within each B-scan is analyzed to determine the vertex of the eye. The eye vertex is tracked over pairs of perpendicular B-scans to determine eye motion. In another embodiment, the decentration in the Pachymetry map is removed by correcting for the misalignment of the center of the Pachymetry map and the actual location of the corneal vertex.

29 Claims, 7 Drawing Sheets

IMAGE ADJUSTMENT DERIVED FROM OPTICAL IMAGING MEASUREMENT DATA

TECHNICAL FIELD OF THE INVENTION

The present invention relates to optical medical imaging, and in particular to systems that are adapted to perform Optical Coherence Tomography ("OCT"), especially as adapted to Anterior Chamber ("AC") imaging in the eye and methods and apparatuses for monitoring and adapting to eye motion in such imaging systems.

BACKGROUND OF THE INVENTION

An optical coherence tomography ("OCT") apparatus is used to perform micron-resolution, cross-sectional imaging of biological tissue. The OCT device uses a light source to illuminate a sample and an interferometer and detector to measure the path length to a reflector in the sample by interference between the light reflected from the sample and a reference light beam. The quality of an OCT image, and the accuracy and reliability of subsequent biometric measurements, depend on proper alignment of the scan lines and/or B-scans of OCT measurement data from which the image is derived.

The proper alignment of the OCT data requires detection and correction of both decentration and eye movement during the scan. Decentration refers to the misalignment between the axis presumed for the measurement and the actual axis of the imaging system. In the prior art, decentration was determined by making a limited number of measurements of known features along different lines of sight. Positioning adjustments are made until the eye is sufficiently aligned before the imaging scan begins. Eye movement refers to the rotation or translation of the eye during the scan. Rotation here refers to rotation of the eye alone and does not include any rotations due to rotational motion of the head. Translation refers to translation of the eye due to translations of the head, wherein the eye moves as a fixture within the head. Eye movement is known to generate artifacts in the displayed image. Most commonly, the target (patient) is requested to remain stationary and, if necessary, scanning is repeated until a sufficiently stationary scan is achieved, with no apparent or at least manageable eye motion.

In surgical applications, particularly laser surgery, knowledge of the position of the target tissue is necessary. Eye motion has been tracked using images of the eye and tracking a feature of the eye (such as the pupil) by detecting the feature and following it from image to image as described in U.S. Pat. No. 7,044,602. Alternatively, special tracking beams illuminate areas or spots on the eye as in U.S. Pat. No. 7,001,377, tracking eye motion by analyzing reflection from the illuminated spots.

Other previous eye tracking devices derive eye motion from other monitored signals. For example, U.S. Pat. No. 5,517,021 discloses an eye tracking apparatus that detects bioelectromagnetic signals generated by the muscles that move an individual's eye while U.S. Pat. No. 5,422,689 discloses an eye-tracking device that monitors electro-oculogram signals produced by eye motion.

One biometric measurement is illustrated in a Pachymetry map. Pachymetry is a test that measures thickness of the cornea of the eye. Traditionally, pachymetry has been measured using ultrasound, which provides a reading of corneal thickness from Bowman's membrane to Descemet's membrane. A Pachymetry map ("PM") is a 2D graph or image showing the thickness of the cornea over an area. Recent advances in Optical Coherence Tomography ("OCT") provide the opportunity to create a PM without requiring the probe-media contact required for ultrasound imaging. Measurement data is collected or received along multiple OCT scan lines that span a 3-D volume and are nominally arranged in multiple planar groups (B-scans). Once the cornea is detected, its thickness can be measured so that, ideally, for each scan line or for some subset of scan lines there is a measurement of the thickness of the cornea along each scan line. Corneal thickness measurements made over scan lines distributed across the cornea can be used to derive a corneal thickness map whose resolution is dependent upon the resolution of the measurement data in the scan lines and the distribution of the scan lines across the eye. Ideally, the corneal vertex is aligned with the center of the scan pattern to avoid decentration errors. In current AC-OCT machines, the center of scan pattern is usually imperfectly aligned with the corneal vertex because of difficulties of attaining and maintaining subject alignment. Decentricity errors are known to create errors in the PM. Studies on PM repeatability reveal that thickness errors of as much as 50 µm can occur in peripheral zones when the corneal vertex is decentered by as little as 1 mm.

While the Pachymetry map is a map of biometric measurements of the corneal thickness in the anterior chamber of the eye, the retinal nerve fiber layer (RNFL) thickness is a biometric measurement in the posterior chamber of the eye. While the techniques described here are generally applied to the anterior chamber, one skilled in the art can apply these techniques to the posterior of the eye and RNFL thickness measurements or measurements of the fovea, for example.

In recent years, requirements for dense scan coverage of the cornea have increased the duration of the exam, thereby compounding the alignment problem. Due to longer scan durations, the probability of eye movement during the scan increases. A method for determining motion during the scan and either automatically eliminating bad scans or correcting the identified bad scans to make them good scans is greatly desired. Furthermore, a method of automatically detecting and correcting decentration is highly desired. Even if the eye were initially properly aligned, after eye movement it is misaligned. Even if it remains stationary after the eye movement, decentration has occurred. Collection of data on the misaligned eye can be used for improved Pachymetry maps if the misalignment can be detected and characterized to the point that the map can be corrected for the decentration. In particular, the present invention satisfies the need to greatly reduce the error in corneal thickness measurement caused by decentration or motion. More generally, the present invention satisfies the need to greatly reduce image artifacts caused by misregistration of scan lines during measurement data collection.

In light of the above, there is a need in the art for method and apparatus to detect eye position from imaging data. For instance, there is a need to minimize the impact that misalignment and eye motion have on OCT imaging scans using only the OCT scan data.

SUMMARY

The present invention is defined by the claims and nothing in this section should be taken as a limitation on those claims.

In accordance with the present invention, a method and apparatus is provided for alignment of scan lines relative to the position of the eye. The image of the eye derived from the scan lines is improved by minimizing misalignment. One means for implementing this improvement is to build the image using a scan pattern comprised of pairs of crossed B-scans to build the image and detecting misalignment for each B-scan or B-scan pair and correctly aligning the image data prior to display. One means for detecting misalignment is by finding a landmark of a structural feature within the measurement data. In the anterior chamber, a structural feature of interest is the cornea. The preferred landmark is the vertex of the cornea.

Initially the Pachymetry map is registered to the center of the scan pattern. One embodiment of the present invention is the detection of the corneal vertex (vertex) and registering (or re-registering) the Pachymetry map to the vertex. The imaging scan lines are initially registered to the imaging device. Proper registration of the scan lines for the Pachymetry map re-registers the scan lines to the eye. The relationship between the highest point (HP) of the corneal arc in each B-scan and the vertex is used to adjust the image to correct for the decentration error and properly display the Pachymetry map. Proper correction improves and ensures repeatability of the thickness measurements.

Another embodiment of the present invention is the detection of eye motion and correction of display data using measurement data collected by an OCT system. The display data is corrected by adjusting elements of the display derived from measurement data, in particular adjusting the registration of the scan lines, by an amount related to the displacement of the scan lines due to the detected motion. Preferably, after detecting the position of the vertex over time, the change in the position of the vertex over time is used to measure motion of the eye.

Still another embodiment of the present invention is the use of a specific scan pattern to minimize motion artifacts. This special scan pattern can be used to create a Pachymetry map from optical imaging data. This scan pattern consists of 8 evenly distributed planar scans (B-scans) with a common central axis whereby sequential pairs of scans are essentially perpendicular.

Still another embodiment of the present invention relates to the selective rejection of scans where large eye movement is detected.

Still another embodiment of the present invention relates to the use of interpolation to improve motion correction.

Still another embodiment of the present invention relates to the application of detection and correction of eye decentration and movement during the scan for both anterior and posterior surfaces of the eye. When examining the posterior of the eye with an OCT imaging device, one useful vertex is that point on the surface of the retinal nerve fiber layer where the OCT beam traverses the longest path length to the imaging device. In the posterior of the eye, a structural feature of interest is the retina.

While previous studies reveal thickness errors of as much as 50 μm when the vertex is decentered by as little as 1 mm, using this new method, we have achieved repeatability of ≦5 μm in central 2 mm zone, and ≦10 μm in 2.5-3.5 mm radial zones for PM measurements. Repeatability in PM measurements is ensured using the geometric relationship between the highest point (HP) in each line scan and the vertex to compensate for the decentration error.

DETAILED DESCRIPTION

Anterior Chamber Optical Coherence Tomography ("AC-OCT") is a state-of-art technology for anterior chamber imaging. AC-OCT can produce a corneal thickness map (Pachymetry map). The Pachymetry map is generally derived from a plurality of B-scans, though, there is no reason that this could not be derived from any sufficiently densely placed collection of scan lines. Most commonly, a B-scan is a collection of scan lines within a plane. A B-scan display is often called a tomogram. The tomogram is derived from measurement data in depth along scan lines and in breadth across the scan plane (the B-scan). AC-OCT measurement data is typically collected along scan lines, where the lines extend from the diagnostic instrument into the eye, with the lines collected across a plane (B-scan).

Figure 1:
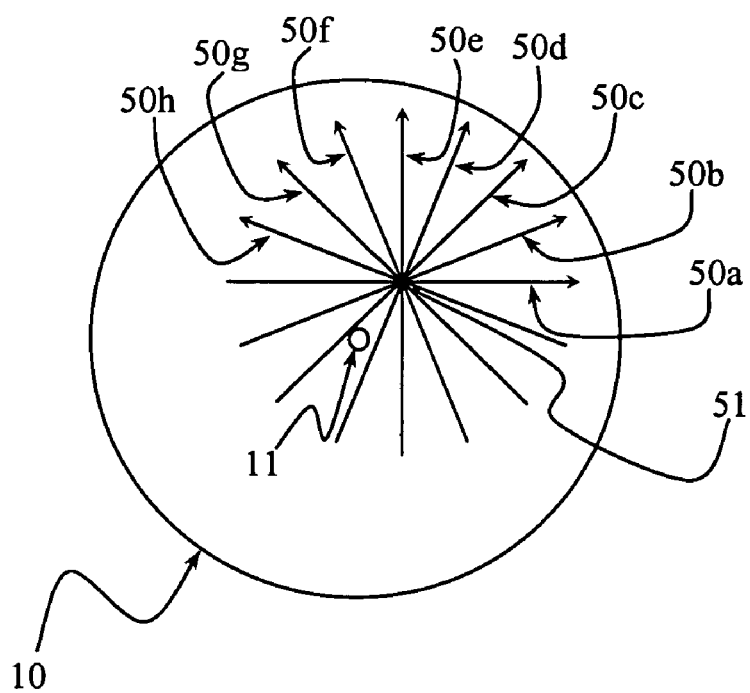
FIG. 1 is a schematic illustration of a projection in the x-y plane of a typical OCT scan pattern for making a Pachymetry map, with labeled scan order, and showing the relationship between the vertex and the center of the scan pattern.

FIG. 1 illustrates, in projection, a typical AC-OCT scan pattern for measuring corneal thickness. This scan pattern is a fan of B-scans intersecting at a common center 51. For more uniform resolution, the B-scans are evenly distributed about their common center. In AC-OCT, it is straightforward to create a Pachymetry map centered at the center of the scan pattern 51. However, the end user reads the Pachymetry map as if it were centered at the point closest to the imaging device, i.e., centered at the vertex 11. In the prior art, the misalignment is minimized by initially aligning the center of the scan pattern 51 to the vertex 11 and thereafter assuming that the alignment is correct. Using a repeatable fixation, the patient is initially aligned to the desired geometry so that the center of the vertex is aligned with the center of the scan pattern 51. A misalignment of the scan is shown by the displacement of the vertex 11 and the center of the scan pattern 51. Decentration errors occur when the difference between the center of the scan pattern and the vertex is not compensated for when computing the Pachymetry map. In our improvement, we first find the vertex 11 and then determine the displacement from the scan pattern center 51 to the vertex 11 and present the end user with a pachymetry map that is centered at the vertex 11.

FIG. 1 also illustrates the temporal order that prior art systems use to acquire B-scans. In the prior art, a scan pattern of 8 scans 50a-50h, is sequenced in temporal order, first 50a, then 50b, then 50c, etc., finally ending in 50h.

The vertex 11 is the location on the cornea where the OCT beam traverses the shortest path length to the imaging device. Thus, the vertex 11 is the highest point of the cornea in imaging systems where the points closest to the imaging device are arranged at the top of the image. As long as the illumination beams are parallel to one another, the position of the vertex on the eye remains fixed (in the eye reference frame) as the eye is translated in the imaging coordinate system. Thus, the vertex position remains fixed on the eye so long as the eye does not rotate.

We use the imaging device coordinate system, since the imaging system automatically registers all measurement data in this coordinate system. In this coordinate system, the z-axis is along the scan direction, the direction from the imaging system to the eye along the beam of light. The x-y plane is, as usual, perpendicular to the z-axis; the x- and y-axes are perpendicular to one another. Clearly, other coordinate systems can be used with the requisite changes in the algorithms to account for the alternate coordinate system.

To first order, the eye is modeled as a sphere of radius approximately 12 mm. The corneal surface is modeled as a section of the surface of the osculating sphere to the cornea at the vertex. The osculating sphere to the cornea at the vertex is the sphere whose radius is the radius of curvature of the cornea at the vertex, with the vertex being a point on the surface of the sphere and the tangent plane to the sphere at the vertex is the same as the tangent plane to the cornea at the vertex. For simplicity, we will call the osculating sphere to the cornea at the vertex the "corneal sphere". The radius of the corneal sphere is approximately 8 mm.

Figure 2:
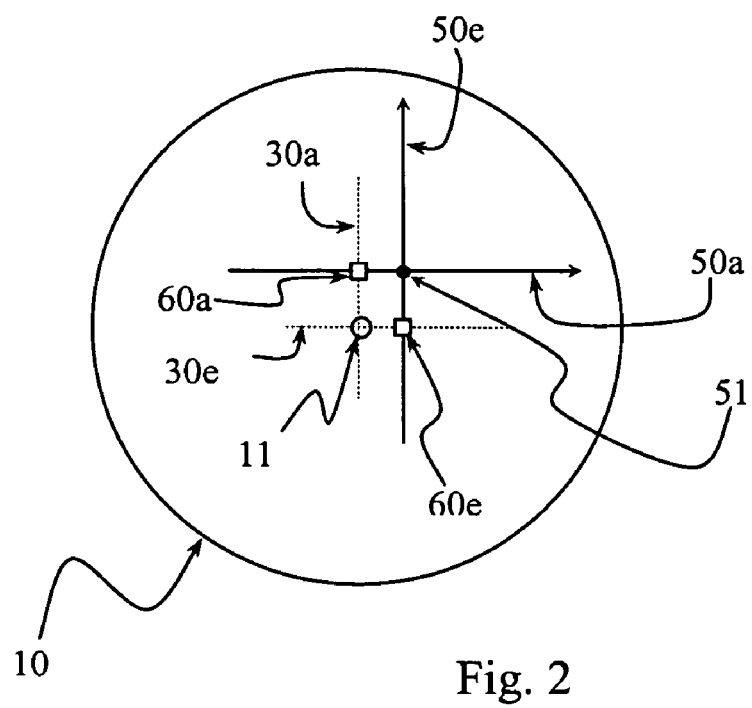
FIG. 2 illustrates the mechanism for estimating the vertex location from measurement data in a pair of perpendicular B-scans.

FIG. 2 illustrates the mechanism for estimating the vertex 11 from B-scans. Two perpendicular B-scans, 50a and 50e, are shown in projection. While ideally 50a and 50e are perpendicular, essentially perpendicular (say, within 10%) B-scans will work almost as well. With decreased accuracy in the estimate, any pair of distinct, non-parallel B-scans can be used, but perpendicular B-scans are preferred. Each B-scan crosses the cornea. Within the tomogram of the B-scan, there is an arc that is the edge of the corneal surface within the B-scan. This arc can be detected using edge detection methods or region detection methods detecting the cornea, and then finding its boundary, or other detection methods known to those skilled in the art. Once the arc is determined or modeled, many parameters of the arc can be determined. Since this arc is smooth, one position parameter of the arc is its radius of curvature at a point. Also, since the arc is smooth and lower at the edges (further from the imaging device) than it is in the central region, it reaches a highest point ("HP") someplace in-between. This HP is another position parameter of the arc. Yet another position parameter is the point in the B-scan plane that is the center of the osculating circle to the arc at the HP. The HP, 60a, of the corneal arc in B-scan 50a is the flat spot along the corneal arc where the arc changes from rising to falling. Analytically, for a smooth arc without inflection points, this is the point where the first derivative is zero.

Decentration errors along the B-scan direction can be detected in the projection plane by comparison of the HP, 60a, and the center of the scan pattern. If there is no decentration error, then the highest point of the corneal arc is at the center of the scan pattern. If the corneal surface is modeled as a section of the surface of the corneal sphere, then each B-scan is a plane intersecting the section of the spherical surface. Such an intersection is a chord; an arc of a circle. Considering the whole of the circle, the line through the center of that circle and perpendicular to the B-scan passes through the center of the corneal sphere. The vertex is the point on the corneal surface directly between the center of the corneal sphere and the imaging device. This is to say that, in the projection plane, the vertex 11 lies on the line 30a perpendicular to the B-scan 50a that passes through the high point 60a of the corneal arc. By applying this technique to a pair of B-scans, the location of the center of the corneal sphere is exposed. The locations of the projection of the vertex, the vertex itself and the center of the corneal sphere are further position parameters of the corneal feature. The projection of the vertex and the projection of the center of the corneal sphere are the same. The actual vertex is the point on the surface of the corneal sphere that is closest to the imaging device, i.e., the point that is the radius of curvature distance from the center in the direction of the imaging device. This can be found using any estimate of the radius of curvature of the cornea.

As shown in FIG. 2, there is a relationship between the HP in each corneal arc and the location of vertex 11. Each B-scan intersects the corneal surface 10 and there is an image of an arc of the corneal surface in each B-scan. The B-scan and the corneal arc projects as a line segments in the x-y plane. In B-scan 50a the corneal arc achieves a peak at 60a, while B-scan 50e images a different part of the cornea (except for the line which is the intersection of the B-scans) and therefore normally has a different HP 60e of the corneal arc. Drawing the line 30a perpendicular to the projection of B-scan 50a and through the projection of HP 60a, and also drawing line 30e perpendicular to the projection of B-scan 50e and through the projection of HP 60e, we see that lines 30a and 30e intersect at the projection of the vertex 11.

The high point of the corneal arc in a typical B-scan can be detected in various ways. One means is to simply take that point which is identified as a part of the cornea which is also closest to the imaging device. This may be computed from the B-scan by image processing techniques. The corneal arc can be detected by thresholding the image to detect the cornea and then determining its boundary or by edge detection techniques to directly detect the boundary of the corneal arc from the B-scan image. A smooth curve can then be fit to the points estimating the corneal arc and the extrema of the fitted smooth curve can be determined using known analytic methods. The smooth curve may be a piecewise polynomial or a local fit of a conic section to portion of the data, preferably an ellipse or a parabola; almost any fit of a smooth curve which is differentiable almost everywhere and has no inflection points can be used. A circle is a special case of an ellipse. The extrema of the fitted smooth curve is the high point whenever the fitted smooth curve is differentiable everywhere, without inflection, and higher in the center than at the edges. The goodness of fit can be measured by least squares or a weighted cost function or one of many other goodness of fit measures known to those skilled in the art. Alternatively, in frequency domain OCT, the closest point to the imager can be determined from envelope peak in the return from the tissue boundary, its underlying frequency, and the correspondence between frequency and depth using either frequency filtering techniques or spectral processing techniques.

FIG. 2 illustrates a technique to estimate the position of the projection of the vertex. Using the technique over time with multiple sets of measurement data, we can estimate the position of the vertex over time. If the eye is stationary, we can improve the estimated position of the vertex, by averaging the position estimates. If the eye has moved, the apparent motion of the vertex provides an estimate of the motion of the eye. To simplify the exposition, we initially limit the exposition to the case where motion is limited to translation in spatial coordinates. If the estimates of the vertex position are within the measurement error inherent in the imaging device, they can be averaged to improve the measurement accuracy of the vertex position. If the estimates of the vertex position are outside of or greater than the measurement error inherent in the imaging device, then motion is present and the movement of the eye can be measured by applying the displacement of the vertex to a model of the physical constraints of the eye.

While the vertex is a convenient point to identify, any geometric equivalent is equally useful. For example, the projection of the center of the corneal sphere in the x-y plane is the same point as the projection of the vertex in the x-y plane. Thus the center of the corneal sphere is geometrically equivalent to the vertex for registering any biometric thickness map, where thickness is measured in the scan direction. Indeed, any fixed point of the corneal sphere is geometrically equivalent under translations when compensating for motion, since the displacement under translation is constant for every point of the sphere.

Given the relationship between the vertex and the center of the corneal sphere, the z coordinate of the vertex is readily obtained from the additional knowledge of the radius of curvature of the cornea at the vertex. Since the center of the corneal sphere and the vertex have the same x- and y-coordinates the z coordinate of the vertex is simply displaced by the radius of curvature of the corneal surface at the vertex toward the imagine device from the center of the corneal sphere. The center of the corneal sphere is equidistant from the two high points, whose coordinates are known. That distance is also the radius of curvature of the corneal surface at the vertex. Given the coordinates of the HPs, the x- and y-coordinates of the center of the corneal sphere and the radius of curvature, the z-coordinate is determined by a quadratic equation in a single variable, whose solution is well known. Once the center is known, the vertex is the same distance from the center as the two measured HPs and in the direction of the scanner.

It is clear to those skilled in the art that other means can be used to find the center of the corneal sphere, such as the least squares method using corneal arc points from at least two different B-scans (different scan planes). Alternate scan patterns may be used to obtain distributions of corneal points from which one can compute the vertex position directly, using least square methods to reduce the impact of noise in position measurements or other methods. However, the preferred method uses very few computational resources and has limited impact on scan patterns. In some cases, using the nominal value of 8 mm for the radius of curvature is sufficient and in other cases a priori knowledge of the corneal radius of curvature exists. In any case, once the two HPs and the radius of curvature are known, the position of the vertex can be determined.

The projection of the vertex is at the point of intersection of the perpendiculars through the projections of the HPs of the two B-scans. The B-scans do not need to be orthogonal to one another. However, since there is a measurement error associated with each HP, the uncertainty in the vertex location can be minimized by maximizing the angle between two B-scans, which yields the preferred nearly orthogonal B-scans. In practice, to further reduce the measurement error, for decentration we use all 4 pairs of B-scans in the scan pattern and average the 4 vertex estimates. Other combinations of the 28 pairs of B-scans in the 8 B-scan scan pattern can be used, with varying results.

Figure 3:
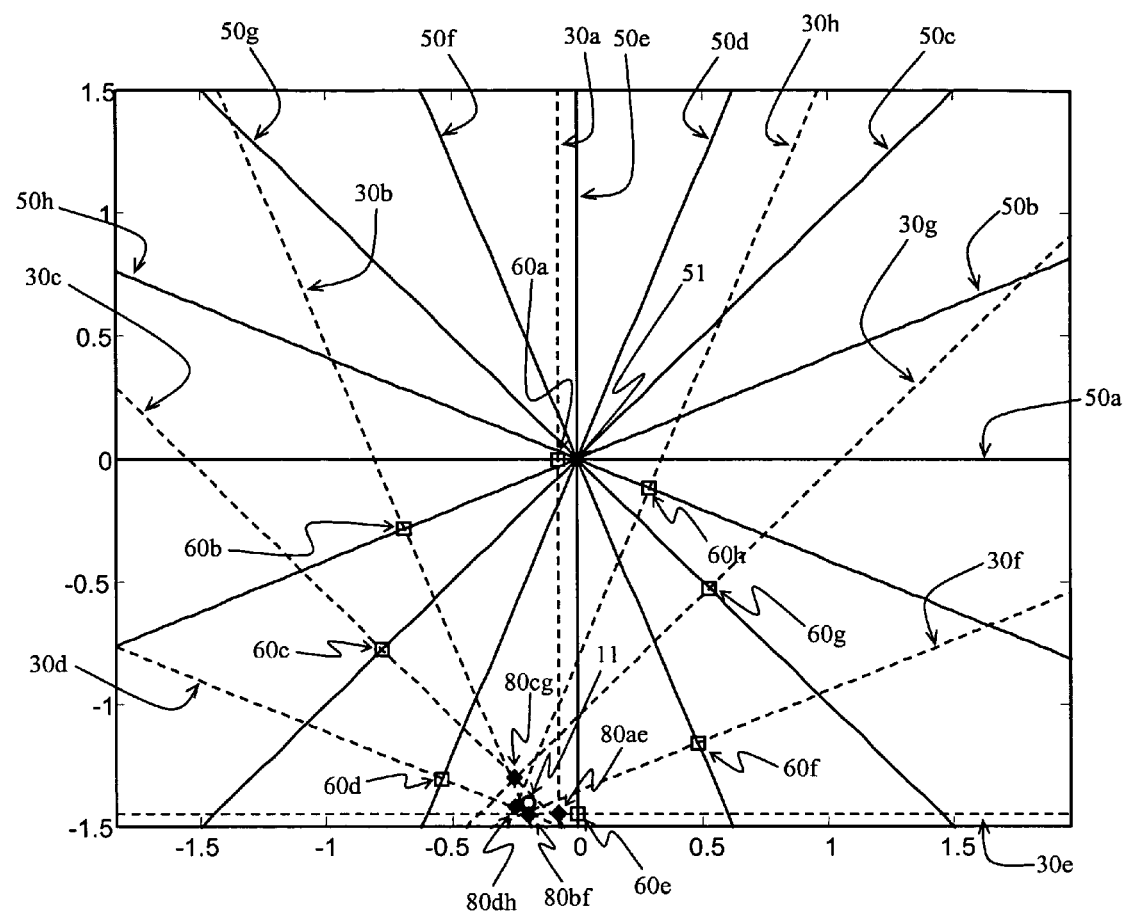
FIG. 3 illustrates the estimated vertex locations using 4 pairs of B-scans.

FIG. 3 illustrates the process for making 4 vertex measurements in the projection plane, $80ae$, $80bf$, $80cg$, and $80dh$. The line $30a$ is perpendicular to the projection of scan plane $50a$ and through the projection of HP $60a$. The line $30e$ is perpendicular to the projection of scan plane $50e$ and through the projection of HP $60e$. The intersection of lines $30a$ and $30e$ is the estimate of the position of the projection of the vertex $80ae$ using corneal arcs $50a$ and $50e$. Similarly the line $30b$ is perpendicular to the projection of scan plane $50b$ and through the projection of HP $60b$. The line $30f$ is perpendicular to the projection of scan plane $50f$ and through the projection of HP $60f$. The intersection of lines $30b$ and $30f$ is the estimate of the position of the projection of the vertex $80bf$ using corneal arcs $50b$ and $50f$. Likewise, the line $30c$ is perpendicular to the projection of scan plane $50c$ and through the projection of HP $60c$. The line $30g$ is perpendicular to the projection of scan plane $50g$ and through the projection of HP $60g$. The intersection of lines $30c$ and $30g$ is the estimate of the position of the projection of the vertex $80cg$ using corneal arcs $50c$ and $50g$. Finally, the line $30d$ is perpendicular to the projection of scan plane $50d$ and through the projection of HP $60d$. The line $30h$ is perpendicular to the projection of scan plane $50h$ and through the projection of HP $60h$. The intersection of lines $30d$ and $30h$ is the estimate of the position of the projection of the vertex $80dh$ using corneal arcs $50d$ and $50h$. Clearly, combinations of other lines could also provide estimates of the vertex location, such as $30a$ and $30c$, or $30a$ and $30d$, etc. Furthermore, once the estimate of the radius of curvature of the cornea is known, an estimate of the vertex position can be obtained by determining the point displaced by the radius of curvature from the center of the corneal sphere along the shortest path to the optics device.

Preferably, averaging vertex position estimates using multiple estimates from multiple B-scan pairs should only be performed when eye motion is not apparent, since significant eye motion between B-scan pairs removes the statistical rational for averaging them, unless they are first corrected for relative motion.

Once the vertex is identified, the center of Pachymetry map can be registered back to the vertex. The map is adjusted by translating components of the display derived from measurement data in particular scan lines or collections of scan lines, such as B-scans, by the displacement of the center of the scan pattern from the vertex at each scan line, collection of scan lines, or B-scan. For simple motion, this correcting procedure can be accomplished using a translation and a 2-D interpolation to match the points of the original Pachymetry map. Once a fixed set of vertex position estimates are made over time; interpolating between known positions or extrapolating from the last known position determines the vertex position at intermediate times. In simple cases, linear interpolation or extrapolation is used. In cases where motion is known to follow a model, as in the case of in some periodic saccadic motion, a fit or best fit to the motion model can be performed and then the resolved motion model can be used in performing the registration. Given only motion data and no a priori knowledge of the motion model, sync interpolation to intermediate values provides intermediate vertex positions. In cases where motion occurs in discrete jumps between B-scans, registration correction is most accurately accomplished B-scan by B-scan. For continuous motion, registration correction is most accurately accomplished scan line by scan line. It is particularly advantageous when registering corrections scan line by scan line to use interpolation to refine the estimated vertex position at the time of the reception of each individual scan line. Faster scan line detection, as seen in spectral domain OCT, provides the opportunity for nearly continuous monitoring of eye position.

Figure 4:
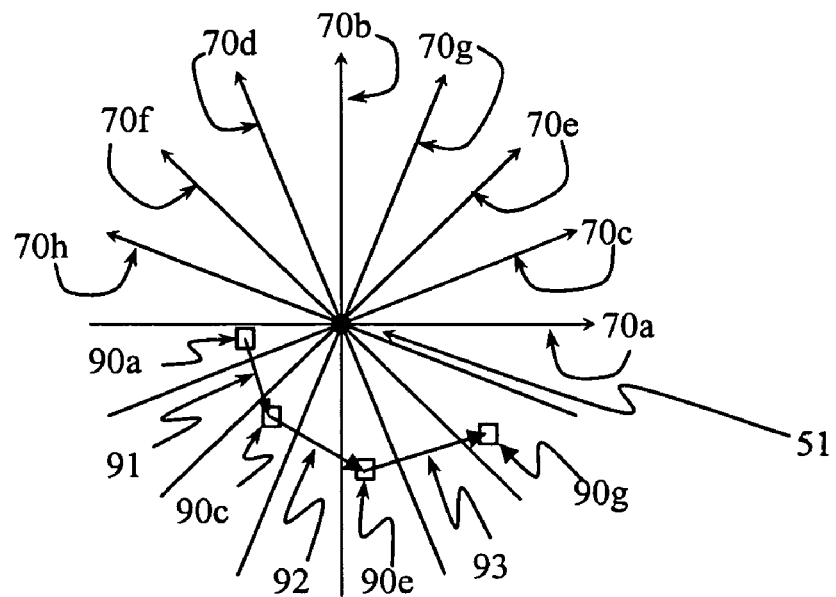
FIG. 4 illustrates a custom scan pattern, using pairs of cross scans, and the resulting vertex estimates.

One error source for the uncertainty of finding the vertex using the above-described method is the latency between the pairs of cross scans. Minimizing the latency (or motion artifacts) is the key to get accurate vertex estimation from each pair. An alternate scan pattern with modified scan order can be employed to minimizing the latency, as shown in FIG. 4. Here the scans $50a$-$h$ are replaced with scans $70a$-$h$. While the new scans are in the same positions as the old scans, the order is changed so that the perpendicular scans are sequentially consecutive. This creates sequential scan pairs ($70a$, $70b$), ($70c$,

70d), (70e, 70f), and (70g, 70h), where the time between perpendicular scans is minimized.

The perpendicular pair scan pattern allows for accurate identification of the vertex. The change in the positions of the estimated vertexes from the four different pairs of cross B-scans is a good indicator of eye movement during collection of the measurement data for the entire scan pattern. If the change in position is within the tolerance of the device's expected measurement error, then no motion has occurred and the positions may be averaged to reduce measurement error. If, however, one or more of the position measurement changes is significantly greater than the expected measurement error, motion has occurred. While the choice of significance varies, a measurement change greater than one standard deviation from the measurement error expected for the system can be chosen to be significant. As shown in FIG. 4, the trajectory of eye movement in the x-y plane can be tracked. The sequentially perpendicular scan pair 70a and 70b provides a measure of the vertex position 90a. The next measure of the vertex position, 90c (made from 70c and 70d) is significantly translated from 90a and the vector 91 provides a measure of the vertex motion. The measure of the vertex position 90e (from 70e and 70f) is again significantly translated from 90c and the vector 92 provides a measure of that motion. Finally, the measure of the vertex position 90g (from 70g and 70h) is again significantly translated from 90e and vector 93 provides a measure of that motion.

As long as the only motion is translation, once the position of the vertex is known relative to any number of B-scans, the B-scans can be registered to one another. Errors in their relative positions due to motion can be corrected and the actual scan pattern exposed. Translating the entire B-scan so that the vertex is aligned compensates for relative motion. The eye motion occurs in a 3-D space. Not only motion in the x-y plane but also in the z-direction (in the direction of a scan line) is detected and compensated. It is important for accurate keratometry and topography measurements based on AC-OCT imaging systems to align the scan lines to account for decentration or motion. With appropriate detection and correction of eye motion artifacts, one can obtain accurate biometric measurements (maps) which are solely limited by the systematic (calibration) errors in positioning OCT scan lines and the anterior surface detection error.

Figure 5:
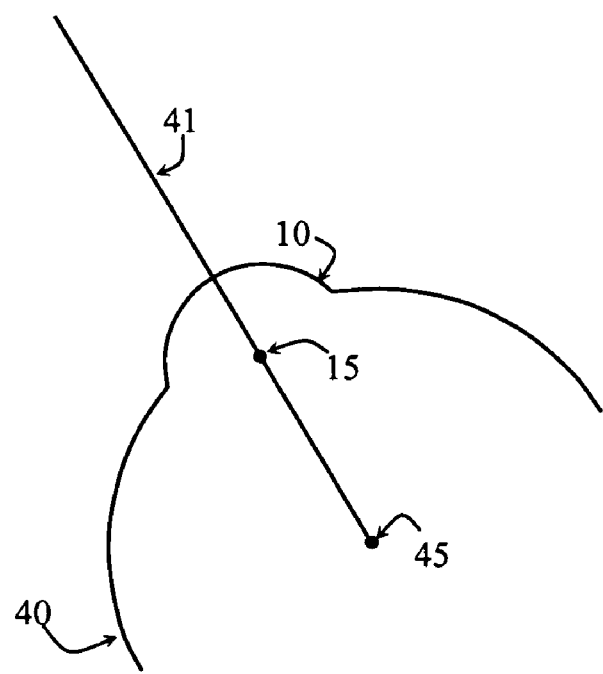
FIG. 5 is an exaggerated illustration of the cornea and eye, and shows that their respective centers lie along the optical axis of the eye.

Turning now to rotations, it is well known that the center of the corneal sphere is not on either axis of rotation of the eye. It is also well known that the radius of curvature of the eyeball is normally greater than that of the corneal sphere. FIG. 5 accentuates this difference for emphasis. The center of the corneal sphere 15 and the center of rotation 45 of the eye 40 lie along the eye's optical axis 41. The eye only rotates with 2 degrees of freedom (rotation about the optical axis is not physically intended), greatly simplifying the task of analyzing arbitrary motion, translation and rotation. This does not account for rotations of the eye due to rotation of the head or the small rotations about the optical axis that can be achieved under duress, such as during surgery because of external forces, or rotations about the optical axis occurring because of imperfections in eye muscles or any other optical axis rotations. Under these conditions, tracking the location of only two points, the corneal center and the center of rotation of the eye, is sufficient to completely describe arbitrary motion of the eye. Of course, any other geometrically equivalent information (for example, information from which these two points can be computed) would also be sufficient.

When correcting biometric maps for misalignment, even less information is needed than the two center points. As long as the rotation is sufficiently small that misalignment of the biometry map can be meaningfully corrected using translation alone, then knowing the position of the vertex alone is sufficient to correct the misalignment. Even though the vertex itself is not a fixed point on the surface, the change in vertex position is proportional to the change in position of a point that is fixed on the surface. The change in the position of a fixed point (say, the point of intersection of the surface of the cornea and the eye's optical axis) is strictly proportional to the change in the vertex position, where the proportionality constant is a function of the radius of curvature of the cornea, and the distance from the center of the corneal sphere 15 to the center of rotation of the eye 45. While in this case, it may be that no fixed component of eye position is known, components corresponding to eye position, namely the change in position, are known. Simply knowing the change in position is sufficient to align scans or track motion.

When more specific information is needed regarding the position of some fixed tissue on the cornea, or a general rotation and translation is modeled, additional information is needed. As discussed above, the corneal arc in a B-scan is lower on the outer edges than it is in the middle. The conjunctiva joins the cornea to the sclera, at which point the surface boundary does not fall away from the imaging device as rapidly as it does along the corneal edge. This is because the radius of curvature of the eye is greater than that of the cornea. Once the center of the corneal sphere and the radius of curvature of the eye are known and the position of the conjunctiva (or the sclera) is known on either side of the cornea in each of a pair of non-coplanar B-scans, the optical axis of the eye can be determined. Any means for determining the radius of curvature of the eye, from a priori information to measurements, is then sufficient for determining the center of rotation of the eye. Given the position of the center of rotation of the eye and the center of the corneal sphere relative to it, the unique position of the eye is determined by a translation of the center of the eye and a rotation about that position.

The center of rotation of the eye can be determined in any of a number of ways. Since the eye is essentially spherical and any collection of non-coplanar points on the surface of a sphere are sufficient to determine the center of the sphere, nominally 4 point on the surface of the eye (not the cornea) are sufficient to determine its center, and also its radius. If a sufficient number of independent points are known, a least squares analysis may also be employed. Since this radius does not change, it can be determined once with special equipment or a special measurement technique, reducing later computations and the need for additional data. This radius can also be computed from certain image data of the conjunctiva when combined with a model of the eye.

Figure 6:
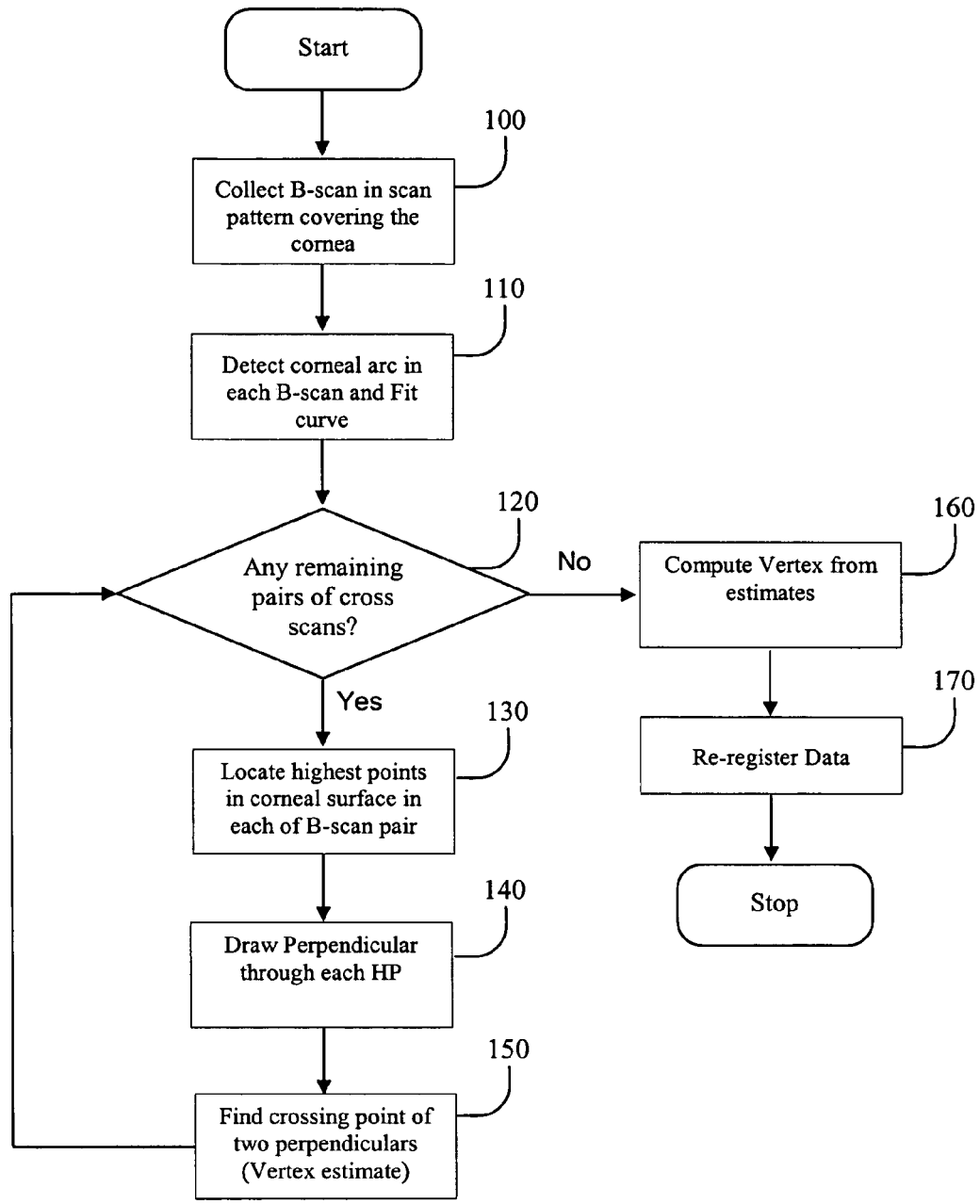
FIG. 6 is an exemplary flow diagram of the present invention for re-registering measurements.

FIG. 6 illustrates one embodiment of a procedure for re-registering measurements using an OCT imaging device. The procedure begins by collecting a plurality of B-scans in act 100. Preferably, the B-scans are paired in sequentially essentially perpendicular pairs and uniformly cover the cornea. They may be collected first and then processed or processing may begin as soon as enough data is available for the next step. For each B-scan, step 110 detects the corneal arc and fits a smooth curve to the arc in the B-scan. Step 120 checks to see if any information remains to be processed. When there are additional B-scan pairs to be processed, step 130 computes the highest points of the corneal edge in each of a pair of B-scans, step 140 determines the perpendiculars through the highest points, and step 150 computes the estimate of the vertex position by finding the intersection of the perpendiculars through the highest points of the corneal edge in the pair of perpendicular B-scans. Once all pairs of B-scans are processed, step 160 computes the measured vertex from the multiple estimated vertex positions. If the estimated vertex positions are averaged to compute the measured vertex, then the scan pattern retains its shape after the B-scans are re-registered; only their location in the coordinate system is displaced and all are displaced the same. However, if it is determined that the eye has moved, re-registration of the B-scans to the vertex displaces some B-scans differently than others, which can affect the shape of the scan pattern. For example, if the B-scans formed a fan of evenly spaced scans about a common axis in the imaging instrument coordinate system, once the vertex position is computed and all of the B-scans are re-registered to the location of the vertex, if the vertex position changes during the scanning interval, the shape of the fan will change and the re-registered B-scans do not necessarily intersect along a common axis. In the case where individual scans are re-registered, their shape in the eye coordinate system might also be different than that in the imaging device coordinate system.

Figure 7:
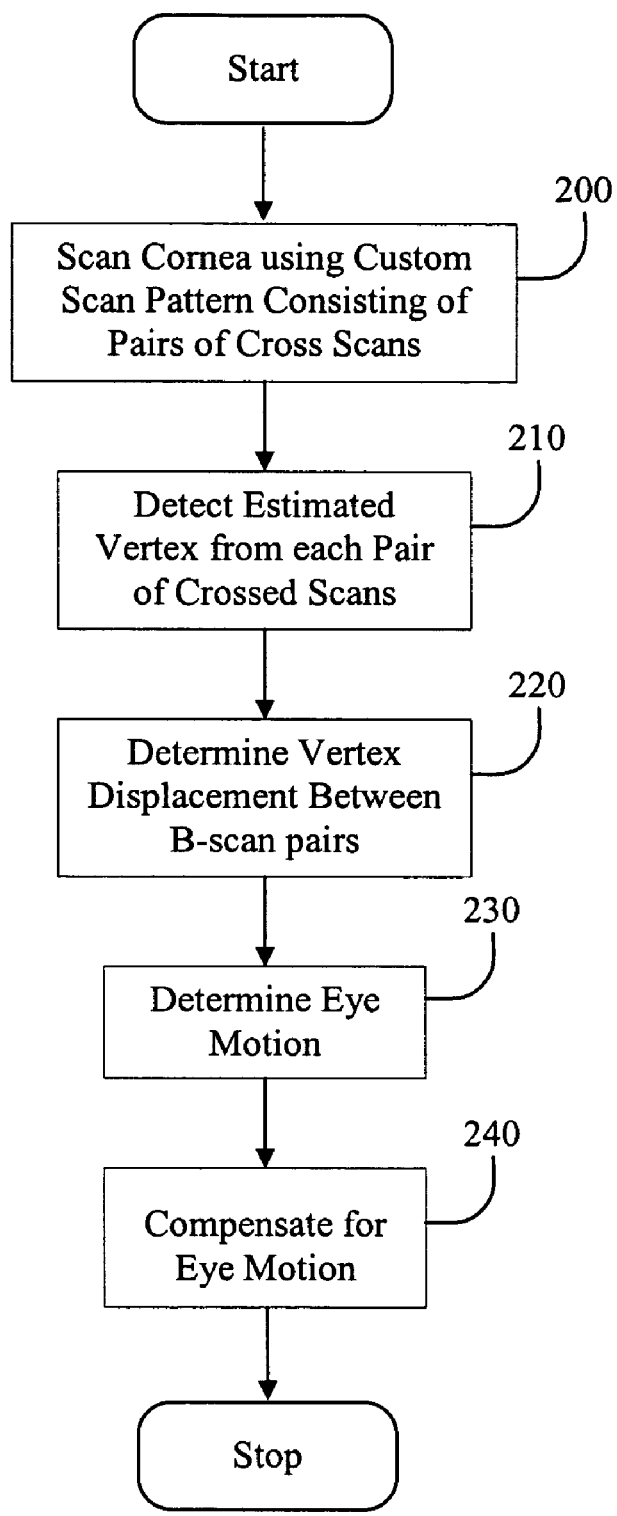
FIG. 7 is an exemplary flow diagram of the present invention detecting and correcting eye motion.

FIG. 7 illustrates one embodiment of a procedure to detect and correct for eye motion. In step 200 we use the custom scan pattern of sequential perpendicular B-scans to collect image data with the property that the vertex estimate from a pair of sequential B-scans over a short time with high accuracy. Perpendicular B-scans maximize the resolution of the vertex estimate while sequential scans minimizes the potential for motion over the duration the data collection period required to acquire the scan pair. In step 210, the vertex position is estimated by determining the position of the intersection of the line perpendicular to the B-scan and through the high point of the corneal arc. In step 220, the positions of the estimated vertexes are compared and vertex displacements are computed. These displacements are used in step 230 to determine the trajectory of the eye motion. Once the eye motion is determined, step 240 compensates for eye motion in image data and biometry maps, such as a Pachymetry map.

Figure 8:
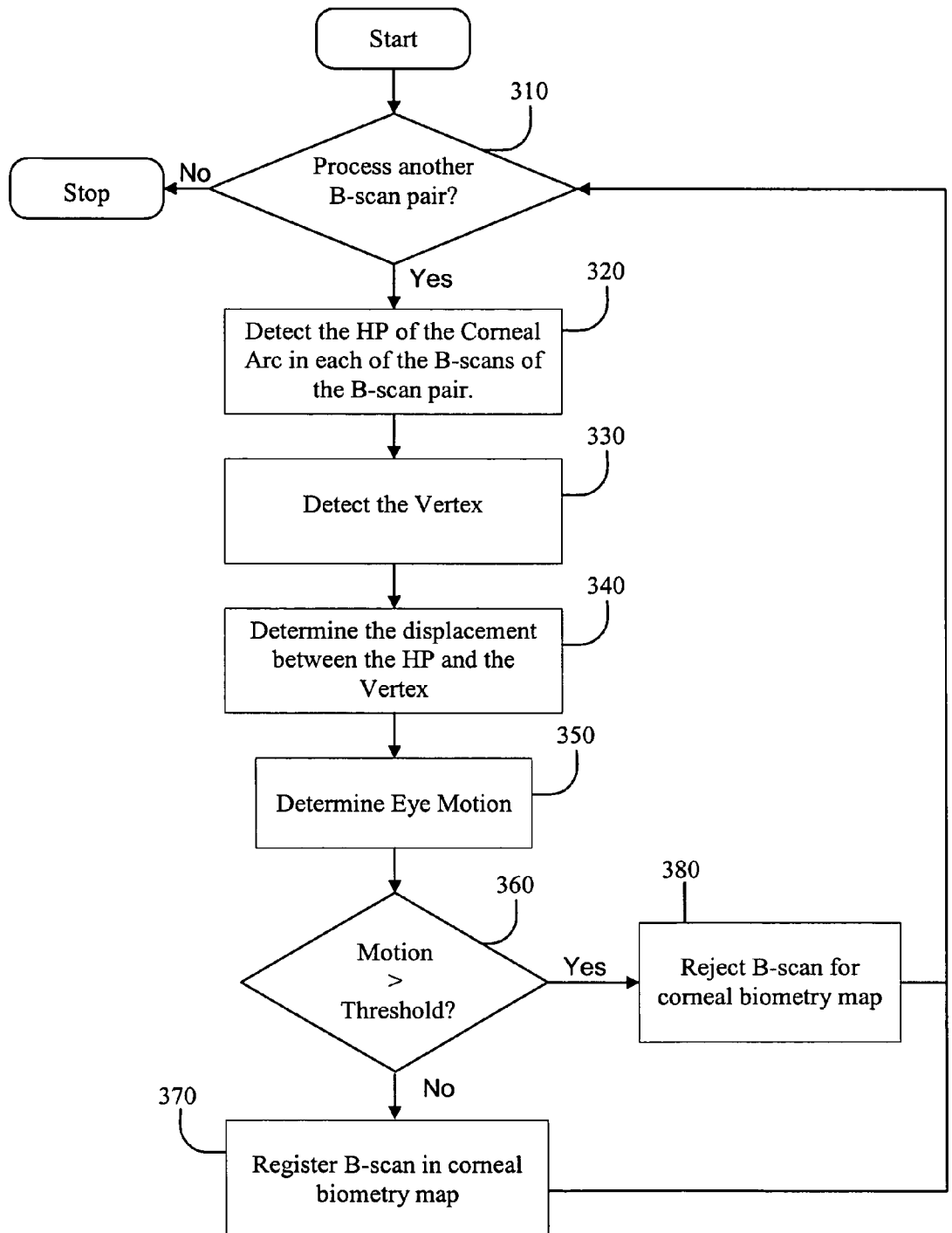
FIG. 8 is an exemplary flow diagram of the present invention detecting and correcting eye motion.
Figure 9:
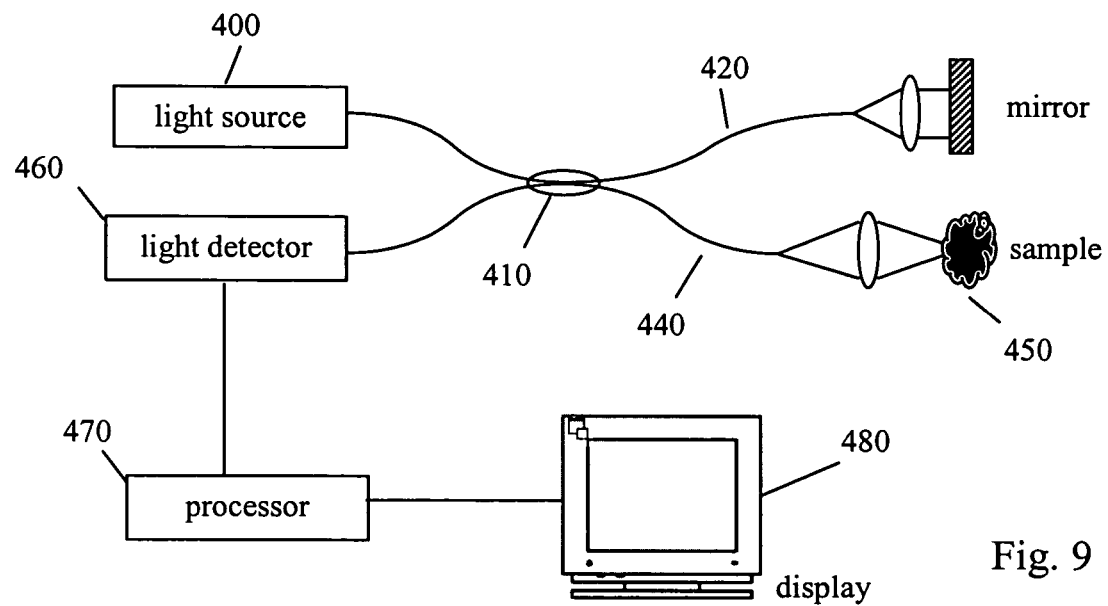
FIG. 9 illustrates an optical coherence apparatus for biometric imaging.

FIG. 8 illustrates a method of registering B-scans to a fixed vertex, rejecting B-scans where motion is greater than a predetermined threshold. In step 310 we determine if there is another pair of B-scans to be processed. If not, then we are finished, but if there is another pair, then in step 320 we detect the high point (HP) of the corneal arc within each B-scan of the B-scan pair. In step 330 we determine the position of the Vertex. In the x-y plane, this is the intersection of the projection of the perpendiculars to the B-scans through the HP of the respective corneal arcs. The z-component of the vertex is the corneal radius from the center of the corneal sphere. After determination of the vertex position, the next step of the process, step 340, is to determine the displacement between each HP of a B-scan and the vertex. Using the displacement of two HPs from the vertex, in step 350 we can determine the motion of the eye. The test, 360, determines if the motion is too great to correct. If the motion is not too large, we implement step 370 and register the B-scan to the vertex so that the biometry data derived from B-scan data is correctly aligned in the biometry map (such as a Pachymetry map). If the motion is too large, we reject the data as in step 380 and do not use it in the biometry map. Once the B-scan pair is registered or rejected, we loop back to step 310 to process remaining B-scans, until complete. figure illustrates only one example and many variations exist and are viable alternative constructions. The example OCT device is comprised of a light source 400 for illuminating a sample 450, a sample optical beam 440, a reference optical beam 420, an interferometer 410 for combining the sample optical beam with the reference optical beam, a detector 470 to detect measurement data from the combined beams, a processor 470 for analyzing the measurement data, and a display 480 for displaying an image of the sample or sample analysis. Other examples of optical coherence apparatuses for biometric imaging are described in U.S. Pat. No. 5,321,501, Swanson, E., et al., "Method and apparatus for optical imaging with means for controlling the longitudinal range of the sample", U.S. Pat. No. 6,053,613, Wei, J., et al., "Optical coherence tomography with new interferometer", U.S. Pat. No. 6,191,862, Swanson, E., et al., "Methods and apparatus for high speed longitudinal scanning in imaging systems", U.S. Pat. No. 6,741,359, Wei, J., et al., "Optical Coherence Tomography Optical Scanner", U.S. Patent Publication No. 2004/0239938 Izatt, Joseph A "System for fourier domain optical coherence tomography", and U.S. Patent Publication No. 2005/0213103 Everett M., et al., "Simple High Efficiency Optical Coherence Domain Reflectometer Design", all of which are hereby incorporated herein by reference. This list of examples is in no way exhaustive and other currently known and unknown examples with the claimed components are envisioned in this apparatus.

The above-described ideas for finding eye motion in the xyz 3D space can be extended to select good scans or correct inadequate scans. This is particularly useful when more line scans are required to achieve denser scan coverage of the cornea for improving the spatial resolution. Bad scans due to large eye movement (against a preset threshold) can be rejected before a map (such as PM map) is created.

Although the main focus has been on the anterior surface, the same ideas can be applied to the posterior surface, because eye moves as a whole piece. Detecting and compensating eye misalignment and movement based on posterior vertex may be particularly beneficial to post-LASIK patients. Among these patients, anterior vertex is no longer readily identifiable due to the refractive surgery. In contrast, posterior vertex should remain largely unchanged.

It should be understood that the embodiments, examples and descriptions have been chosen and described in order to illustrate the principals of the invention and its practical applications and not as a definition of the invention. Modifications and variations of the invention will be apparent to those skilled in the art. The scope of the invention is defined by the claims, which includes known equivalents and unforeseeable equivalents at the time of filing of this application.

The following references are hereby incorporated herein by reference.

U.S. PATENT DOCUMENTS

U.S. Pat. No. 7,044,602 Chernyak, "Methods and systems for tracking a torsional orientation and position of an eye"

U.S. Pat. No. 7,001,377 Li, "Optical tracking system and associated methods"

U.S. Pat. No. 6,749,302 Percival, et al., "Afocal position detection system and ophthalmic instrument employing said system"

U.S. Pat. No. 6,741,948 Hauger, et al., "Method and apparatus for fixing a location"

U.S. Pat. No. 6,669,340 Percival, et al., "Alignment system for an ophthalmic instrument"

U.S. Pat. No. 6,325,512 Wei, "Retinal tracking assisted optical coherence tomography"

U.S. Pat. No. 6,220,706 Foley, "Method and apparatus for determining position of an eye"

U.S. Patent Publication No. 2006/0164653 Everett et al., "Method of motion correction in optical coherence tomography imaging"

OTHER PUBLICATIONS

Hammer D X, Ferguson R D, Magill J C, Paunescu L A, Beaton S, Ishikawa H, Wollstein G, Schuman J S. (2005).

"Active retinal tracker for clinical optical coherence tomography systems." J Biomed Opt. Mar.-Apr. 10, 2005 (2):024038

Ronald Krueger, Raymond Applegate, Scott MacRae "Wavefront Customized Visual Correction: The Quest for Super Vision II" Chapter 24, "Eye Tracking and Alignment in Refractive Surgery: Requirements for Customized Ablation." Taylor N, et al.

What is claimed is:

1. A method of generating an image of an eye from measurement data collected using an optical imaging device comprising:
   (a) collecting measurement data along a plurality of scan lines;
   (b) identifying a structural feature within the eye based on the measurement data;
   (c) determining a plurality of position parameters associated with the identified structural feature;
   (d) analyzing the position parameters to determine a location associated with the structural feature, said location corresponding to one of a vertex, a projection of the vertex and geometrical equivalents thereof;
   (e) adjusting the coordinates of the measurement data based on the determined location; and
   (f) creating an image using at least a portion of the adjusted measurement data.

2. A method as recited in claim 1, wherein the location is tracked over time.

3. A method as recited in claim 1, wherein at least a portion of the measurement data is rejected due to the determined location exceeding a threshold.

4. A method as recited in claim 1, wherein the adjusting step is a spatial correction of the image coordinates.

5. A method as recited in claim 4, wherein interpolation is used to improve the image adjustment.

6. A method as recited in claim 4, wherein the image is a Pachymetry map, which is adjusted for eye misalignment.

7. A method of deriving a component corresponding to eye position from measurement data collected using an optical imaging device comprising:
   (a) collecting a plurality of B-scans imaging a structural feature;
   (b) identifying a first point corresponding to an extrema of the feature in a first B-scan;
   (c) identifying a second point corresponding to an extrema of the feature in a second B-scan;
   (d) computing a first perpendicular to the first B-scan through the first point;
   (e) computing a second perpendicular to the second B-scan through the second point; and
   (f) determining the intersection of the first and second perpendiculars in a projection plane to derive a component corresponding to eye position.

8. A method as recited in claim 7, wherein steps (a)-(f) are performed two or more times.

9. A method as recited in claim 8, wherein successive position components are used to track eye motion.

10. A method as recited in claim 9, wherein successive vertex positions are used to correct for misalignment of the Pachymetry map.

11. A method as recited in claim 7, wherein the plurality of B-scans are evenly distributed about a center point.

12. A method as recited in claim 11, wherein successive B-scans are essentially perpendicular.

13. A method as recited in claim 12, wherein there are 8 B-scans.

14. A method as recited in claim 7, the component of eye position is the component of the vertex along the scan axis.

15. A method as recited in claim 7, wherein the optical imaging device is an optical coherence tomography imaging device.

16. A method as recited in claim 7, wherein the structural feature is the anterior surface of the cornea.

17. A method as recited in claim 7, wherein the component of eye position is the projection of the vertex.

18. A method of registering biometric map data of the eye using an optical coherence tomography imaging device comprising:
   (a) collecting measurement data along a plurality of scan lines imaging a structural feature;
   (b) analyzing the measurement data to determine a location associated with the structural feature, said location corresponding to one of a vertex, a projection of the vertex and geometrical equivalents thereof; and
   (c) registering the biometric map data for the plurality of scan lines as a function of the determined location.

19. A method as recited in claim 18, wherein the biometric map is a Pachymetry map.

20. A method as recited in claim 19, wherein the adjustment corrects for misalignment between a scan pattern generated by the scan lines and the vertex.

21. A method as recited in claim 18, wherein the biometric map data is registered to the vertex scan line by scan line.

22. A method as recited in claim 19, wherein the registering step utilizes interpolated positions of the vertex.

23. A method as recited in claim 18, wherein steps (a)-(c) are performed two or more times.

24. A method as recited in claim 23, wherein the registration function is a translation by a constant multiple of the change in vertex position.

25. A method as recited in claim 24, wherein the constant multiple is greater than 1.

26. A method as recited in claim 25, wherein the biometric map is corrected for eye rotation.

27. An optical coherence apparatus for biometric imaging comprised of:
   (a) a light source for illuminating at least one feature within a sample;
   (b) a sample optical beam reflected from the sample;
   (c) a reference optical beam;
   (d) an interferometer for combining the sample optical beam with the reference optical beam;
   (e) a detector to detect measurement data from the combined beams;
   (f) a processor for analyzing the measurement data to determine a location associated with a structural feature within the eye, said location corresponding to one of a vertex, a projection of the vertex and geometrical equivalents thereof; and
   (g) a display for displaying an image spatially adjusted as a function of the determined location.

28. An apparatus as recited in claim 27, wherein the optical imaging apparatus is optimized for viewing an anterior surface of the eye.

29. A apparatus as recited in claim 27, wherein the optical imaging apparatus is optimized for viewing a posterior surface of the eye.

* * * * *